United States Patent [19]
Wilson, II et al.

[11] Patent Number: 6,047,412
[45] Date of Patent: Apr. 11, 2000

[54] REMOTELY CONTROLLED FILM ADVANCE SYSTEM FOR GOGGLES

[76] Inventors: George P. Wilson, II; Randa M. Wilson, both of 1705 Chisholm Rd., Florence, Ala. 35630

[21] Appl. No.: 09/255,734

[22] Filed: Feb. 23, 1999

Related U.S. Application Data

[60] Provisional application No. 60/080,391, Apr. 2, 1998.
[51] Int. Cl.⁷ ........................................ A61F 9/02
[52] U.S. Cl. ..................................... 2/438; 2/422
[58] Field of Search .................... 2/9, 422, 438, 2/8, 10, 435, 424, 429, 431, 441, 434; 351/47

[56] References Cited

U.S. PATENT DOCUMENTS

| | | |
|---|---|---|
| 1,994,103 | 3/1935 | Huey . |
| 2,259,680 | 10/1941 | Caudell . |
| 2,485,117 | 10/1949 | Settle . |
| 2,886,819 | 5/1959 | Uphoff . |
| 3,946,442 | 3/1976 | Wallander . |
| 4,428,081 | 1/1984 | Smith . |
| 4,748,697 | 6/1988 | Hodnett . |
| 5,163,185 | 11/1992 | Hodnett . |

*Primary Examiner*—Diana Oleksa
*Assistant Examiner*—Katherine Moran
*Attorney, Agent, or Firm*—Richard C. Litman

[57] ABSTRACT

An automatic remotely-controlled film-advancing system clipped onto goggles for continual clear vision through the goggles by a driver of a motorcycle or an all terrain vehicle. The film is advanced from a supply canister to a take-up canister over the goggles by a motor, responsive to a receiving control box receiving signals from a remote transmitter element located on a vehicle handlebar, and manually controlled by a push button.

3 Claims, 1 Drawing Sheet

REMOTELY CONTROLLED FILM ADVANCE SYSTEM FOR GOGGLES

CROSS-REFERENCE TO RELATED APPLICATION

This application claims the benefit of U.S. Provisional patent application Ser. No. 60/080,391, filed Apr. 2, 1998.

BACKGROUND OF THE INVENTION

1. Field of the Invention

The present invention relates generally to a film-advancing, clip-on system for goggles for maintaining clear vision through the goggles worn by a driver on a motorcycle, an all terrain vehicle (ATV) or the like. Specifically, the flexible transparent film is advanced from a supply canister to a take-up canister over the goggles by a motor and receiving control box remotely controlled by a push button transmitter element clamped on a handlebar of the vehicle.

2. Description of Related Art

The related art of interest describes various means for cleaning or defogging a visor on a driver's helmet. However, not one reference describes the maintenance of clear vision of goggles with a remotely controlled hand control. The related art will be discussed in the order of perceived relevance to the present invention.

U.S. Pat. No. 4,428,081 issued on Jan. 31, 1984, to Robert E. Smith describes a motorcycle or painting goggle with a renewable protective surface. A supply magazine holds a protective film which is manually advanced to a take-up magazine for receiving and holding the spent film. The advancing ratchet and pawl mechanism is located in the bottom of the take-up magazine and actuated by pulling out a knob (with the left hand) attached to a flexible cord. The motorcycle goggle with the renewable protective surface is distinguishable for having a manual advance system requiring the left hand to leave the handle bar for advancing the protective film.

U.S. Pat. No. 2,886,819 issued on May 19, 1959, to Joseph H. Uphoff describes a pair of goggles integrated with a double reel system to clean each eye portion with an outside take-up reel and an inner supply reel. The transparent lens material is advanced for each eye by manually manipulating the roughened flanges of the outer take-up reel. The unitary goggles and lens system is designed for use when painting (brush and spray), dusting and grinding. The pair of goggles is distinguishable for its unitary structure and automatic control by a remote activator as in the present invention.

U.S. Pat. No. 3,946,442 issued on Mar. 30, 1976, to Bengt O. H. Wallander describes a helmet visor attachable to a crash helmet. The visor comprises an innermost curved transparent plate, an optional intermediate antifriction layer, and an outer movable film. A take-up roll in a cylinder is energized by a motor which runs continuously or is connected by leads to a bite contact which controls the movement of the outer film. An accumulator or a battery supplies the power, but its location is not shown. The supply roll is positioned on the opposite side. The film rolls can be located to move the film vertically or horizontally. A fixed wiper blade is located in front of the take-up roll for scraping away deposits. The visor apparatus is distinguishable for its requirement for attachment to a helmet rather than to goggles.

U.S. Pat. No. 4,748,697 issued on Jun. 7, 1988, to Jack L. Hodnett describes a face mask with several interchangeable lens made of polycarbonate or acetate for painting or sandblasting. A soft rubber or plastic cowl is provided with a track insert having a pair of tracks spanning an open lens window. When a new lens is required, the user pulls out the dirty lens from a canister and tears along a perforated line for separating lenses to discard the used lens. The face mask is distinguishable for its manual separation of lenses and the use of only one supply canister.

U.S. Pat. No. 5,163,185 issued on Nov. 17, 1992, to Jack L. Hodnett describes a similar helmet for painting or sandblasting having three curved tracks defining a common lens window with a canister supplying a new lens. The helmet is distinguishable for its manual separation of lenses and the reliance on only one supply canister.

U.S. Pat. No. 1,994,103 issued on Mar. 12, 1935, to James G. Huey describes an aluminum face protector casing with a head harness to space the casing with two adjacent sight openings from the face. A 1.5 mils thick cellophane film is supplied manually from a supply cylinder across the openings to a take-up cylinder with an upwardly protruding operating bar. The face protector is used when spraying tar or paint. The face protector is distinguishable for its open face, manual operation and the use of cellophane which would not withstand the wind force involved in driving.

U.S. Pat. No. 2,259,680 issued on Oct. 21, 1941, to William S. Caudell describes a workman's protective paper hood which is clamped onto the head with a head clamping frame, a paint filtering system, and a cloth neck shield with drawstring for protection during spray painting. A horizontally arranged V-shaped web casing member covers the open window of the paper hood. Another four-sided frame member is snapped onto the V-shaped web casing member having a supply reel on one end and a take-up reel with a crank on the opposite end. The movable web is cellophane which is supported by four rollers to maintain the sheet in channels of the four-sided frame member. The hood and double reel apparatus is distinguishable for its paper hood combination and the requirement of manual control.

U.S. Pat. No. 2,485,117 issued on Oct. 18, 1949, to Frank E. Settle describes a painter's mask having a front mask attached to a hood. The flat front portion of the mask has a rectangular opening covered by a cellulose film supplied vertically from an upper casing to a take-up spool having a turning key in the lower casing. Both casings are hinged and spring clipped to the mask. The painter's mask is distinguishable for requiring a mask of a specific structural configuration, a manually operated vertical operation of the moving film and a supporting hood.

None of the above inventions and patents, taken either singly or in combination, is seen to describe the instant invention as claimed.

SUMMARY OF THE INVENTION

The present invention is an automatic remotely controlled film advancing system for keeping goggles clear of dirt for a driver on a motorcycle, an all terrain vehicle (ATV) or the like. The film advancing portion is clipped onto the goggles. The film is advanced from a supply canister to a take-up canister over the goggles by a motor and control box receiving signals from the transmitter control with a push button switch, the transmitter control box being positioned on a handlebar of the vehicle.

Accordingly, it is a principal object of the invention to provide an automatic remotely controlled film advancing system for goggles subject to dirt accumulation.

It is another object of the invention to provide an automatic remotely controlled film advancing system clipped onto goggles and having a take-up canister and a supply canister for the film.

It is a further object of the invention to provide an automatic remotely controlled film advancing system for goggles having a motor and a control receiver located adjacent to the take-up spool.

Still another object of the invention is to provide an automatic remotely controlled film advancing system for goggles having a push button transmitter control located on a handlebar.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
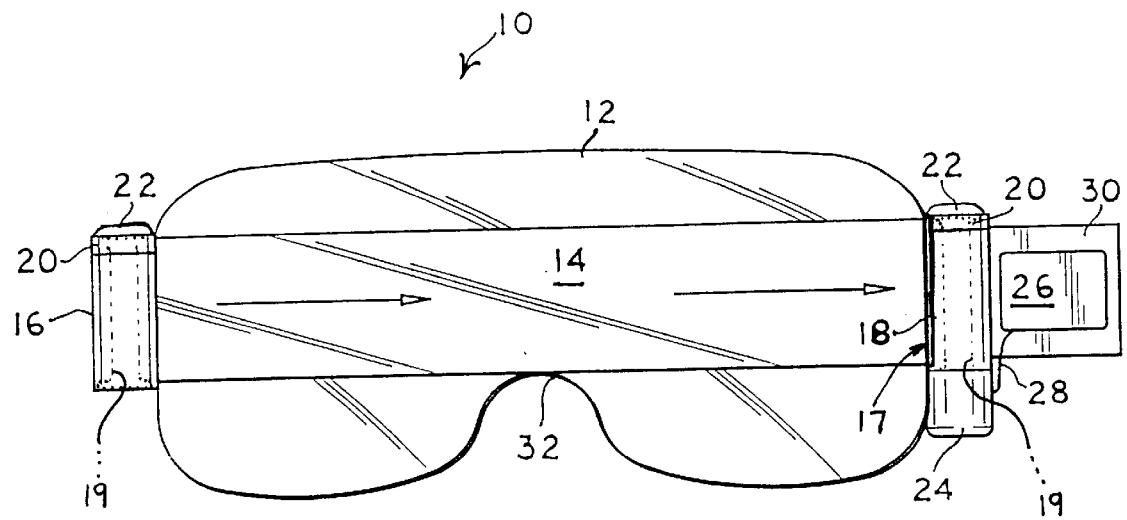
FIG. 1 is a largely diagrammatic, front elevational view of a remotely controlled film advance system for goggles according to the present invention.

In FIG. 1, the present invention, a remotely controlled film advance system 10 is shown positioned on an exemplary pair of framed goggles 12 with the goggles' strap not shown. The flexible plastic and transparent strip of film 14 advances across the main portion of the goggles 12 by being pulled from a supply canister 16 into a take-up canister 18. Each canister 16, 18 has a cap 20, a clip 22 (partially shown) for attaching to the goggles' strap, and the film 14 on a spool 19. An electric motor 24 is integrated with the take-up spool and activated by a radio wave receiver unit 26 through a conducting wire 28. The receiver unit 26 is positioned on a tab 30 integrated with the canister 18.

It should be noted that the film 14 does not cover the entire surface of the goggles 12, due to presence of the notch 32 for accommodating the nose in the lower region and the upper region above the eyes. It has been found that the protected region of the goggles 12 is adequate to maintain clear vision for the wearer. If the dirt coating the film 14 is thick, a narrow slit 17 of the take-up canister 18 will scrape off excessive dirt.

Figure 2:
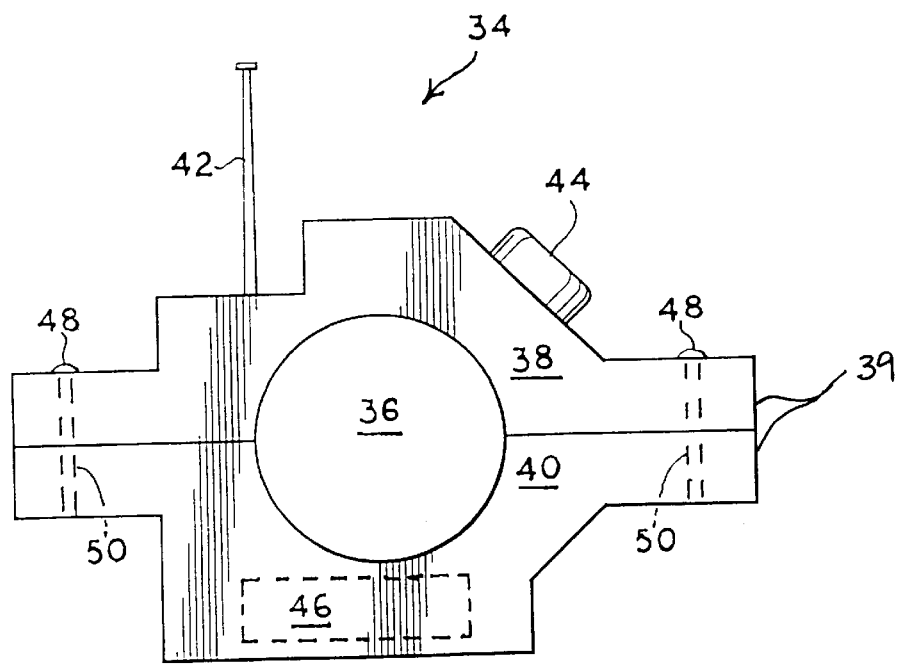
FIG. 2 is a side elevational view of a transmitter control element for attachment to a motorcycle handle bar, according to the present invention.

In FIG. 2, the remote control transmitter unit 34 is depicted as adapted for removably clamping onto a handlebar of a cycle. A bipartite housing 39 for the transmitting components of the transmitter 34 has an upper portion 38 and a lower portion 40. The upper portion 38 has a transmitting antenna 42, preferably flexible and rubber coated, and an activating push button 44 in the rear. The lower portion 40 mates with the upper portion 38 to complete a substantially waterproof and dirtproof housing. The upper and lower portions 38 and 40, respectively, each have a generally semicircular channel defined centrally, and, when clamped together, mate to form a generally cylindrical passage 36 which is sized to closely fit a cycle handlebar. The two portions 38,40 are joined by fasteners 48, preferably traversing through-bores 50 defined in the upper and lower portions which align in registry to accept fasteners 48.

The transmitter 34 is energized by a battery 46 (shown in broken line) housed in the lower portion 40. The wiring connections, push button switch 44 and circuitry in the transmitter 34 are conventional and may be engineered by one skilled in the art to supply a signal on an intermittent and selective basis responsive only to the depression of the push button switch 44. Thus, a driver of a motorcycle, an all terrain vehicle, or any similar open vehicle can maintain their hands on the handlebars while traveling over dusty or muddy terrain, and yet maintain a clear vision through the goggles by operating the push button 44. The push button activates the transmitter 34 which sends the activation signal to the radio wave receiver unit 26, which in turn activates the electric motor 24 for the duration of the pulse, or, alternatively and preferably, for a predetermined duration corresponding to one or more rotations of the spool which advances a predetermined length of film. The motor 24 may be chosen from miniaturized servo-motors known in the art having a rotating drive spindle, and, subsequently affixed by its drive spindle to the takeup spool 19.

It is to be understood that the present invention is not limited to the sole embodiment described above, but encompasses any and all embodiments within the scope of the following claims.

We claim:

1. A remotely controlled film advance system for maintaining clean goggles for a driver of an open vehicle with handlebars comprising:

a first component structure comprising a supply canister with a clip containing a transparent film, a take-up canister with a clip and an electric motor for advancing said film, and a radio wave receiving unit attached to said take-up canister for energizing said motor, said film traversing a pair of goggles horizontally; and a second component structure comprising a radio wave transmitting element having an upper portion and a lower portion adapted to clamp onto a handlebar, said upper portion containing an antenna and a push button control and said lower portion containing a battery;

whereby said clips of said first component are attached to straps of said pair of goggles for moving said film when dirtied across the goggles by remote control from said transmitting element, thus to move dirtied film into said take-up canister and supply fresh film across said goggles, thus to maintain a clear vision through said goggles.

2. The system according to claim 1, there further being a tab integral with said take-up canister, said receiving unit be located on said tab integral with said take-up canister.

3. The system according to claim 1, wherein said transparent film is plastic and flexible.

\* \* \* \* \*